United States Patent [19]
Trawöger et al.

[11] Patent Number: 5,651,673
[45] Date of Patent: Jul. 29, 1997

[54] VIBRATION-DAMPING SUPPORT FOR A DENTAL SEPARATOR

[76] Inventors: Werner Trawöger, Huebe 26; Bruno Pregenzer, Huebe 30, both of A-6173 Oberperfuss, Austria

[21] Appl. No.: 532,592
[22] PCT Filed: Mar. 21, 1994
[86] PCT No.: PCT/AT94/00030
§ 371 Date: Sep. 29, 1995
§ 102(e) Date: Sep. 29, 1995
[87] PCT Pub. No.: WO94/22392
PCT Pub. Date: Oct. 13, 1994

[30] Foreign Application Priority Data

Mar. 30, 1993 [AT] Austria .................................. 637/93

[51] Int. Cl.⁶ ............................ A61C 17/06; A61C 17/14
[52] U.S. Cl. ................................................................ 433/92
[58] Field of Search .......................................... 433/91, 92

[56] References Cited

FOREIGN PATENT DOCUMENTS 8904641  6/1989  WIPO.

*Primary Examiner*—Nicholas D. Lucchesi
*Attorney, Agent, or Firm*—Herbert L. Lerner; Laurence A. Greenberg; Werner H. Stemer

[57] ABSTRACT

The dental separator with an inlet, an outlet and a centrifuge has a vibration-damping support. The support is formed with line connections and each inlet and outlet of the separator is inserted into the support and communicates with a line connection of the support. The support of the invention has two parts. The first part can be mounted in stationary fashion and can be disposed removable on the second part of the separator. The two parts are joined together with vibration-damping intermediate components.

11 Claims, 2 Drawing Sheets

VIBRATION-DAMPING SUPPORT FOR A DENTAL SEPARATOR

BACKGROUND OF THE INVENTION

1. Field of the Invention

The invention relates to a vibration-damping support for a dental separator, which has at least one inlet, at least one outlet, and a centrifuge, wherein the support is provided with line connections, and each inlet and outlet of the separator inserted into the support communicates with a line connection of the support.

2. Description of the Related Art

A support of this kind can be found for instance in International Patent Disclosure WO 89/04641. The separator shown there comprises two partial units; one part, which separates suction air from the mixture and decants solids in the collection container, can be pulled out in drawerlike fashion from the support. The second part includes a centrifuge, whose inlet and outlet communicates via elastic pieces of tubing with the line connections of the support, and which rests on a bearing plate. After the removal of the elastic pieces of tubing the centrifuge can be removed at the top. This is relatively complicated, and it is the object of the present invention to embody a support of the type referred to at the outset in such a way that the separator is easier to remove.

SUMMARY OF THE INVENTION

According to the invention, this is attained in that the support has two parts, wherein the first part can be mounted in stationary fashion and can be disposed removably on the second part of the separator, and that the two parts are jointed together by means of vibration-damping intermediate components. Since the vibration-damping intermediate components are thus components of the support, the separator can be removed from the second part of the support, to which it is fixed by arbitrary connecting means.

The two parts of the support are manufactured in particular from a first plastic, for instance a polyamide or a polypropylene, and preferably embodied essentially in the shape of a U. The vibration-damping intermediate components are in particular of a polyamide- or polypropylene-based thermoplastic elastomer, which can be processed in injection molding systems together with the first plastic to make a one-piece product.

Preferred embodiments contemplate that at least one vibration-damping intermediate component is embodied as an elastic tube section or as a movably disposed rigid tube section between an aperture, associated with an inlet or outlet of the separator, in the second part and a line connection in the first part of the support, so there is no need to open any tubing couplings, either.

The support and the separator in this embodiment form an extremely compact unit that requires the least amount of space, and a further preferred embodiment contemplates that the side ridges of the U-shaped inner part form a lateral guide for a separator that can be pulled out in drawerlike fashion.

If retaining tabs which can be engaged from behind for a tightening lever closure are formed on the free ends of the U-shaped inner part of the support, and/or if the side ridges of the U-shaped inner part have tight-fit faces that converge in the direction of removal of the separator and that can be engaged around the outside by corresponding elements of the separator housing, the result after the insertion of the separator is then a tight communication between each inlet or outlet and the line connection of the support. Optionally, the mouth of the tube section can be equipped with an O-ring. Alternatively, it is contemplated that a sealing ring of the elastomer of the pipe section is coextruded on the inner portion of the support in the region of the mouth of the tube section.

The options for mounting the separator are greater if at least one elastic tube section is disposed in a corner region of the support and communicates with two line connections pointing in different directions. An unneeded line connection is closed off by a stopper.

The side ridges of the approximately U-shaped outer part, mounted in stationary fashion, can also extend obliquely at an angle of 45°. Connection components with a 45° angle can then be inserted rotatably into the line connections, so that lines that extend onward can assume all the positions between the horizontal and the vertical.

The invention will now be described in further detail below in conjunction with the figures of the accompanying drawings, but is not limited thereto.

DESCRIPTION OF THE PREFERRED EMBODIMENT

Figure 1:
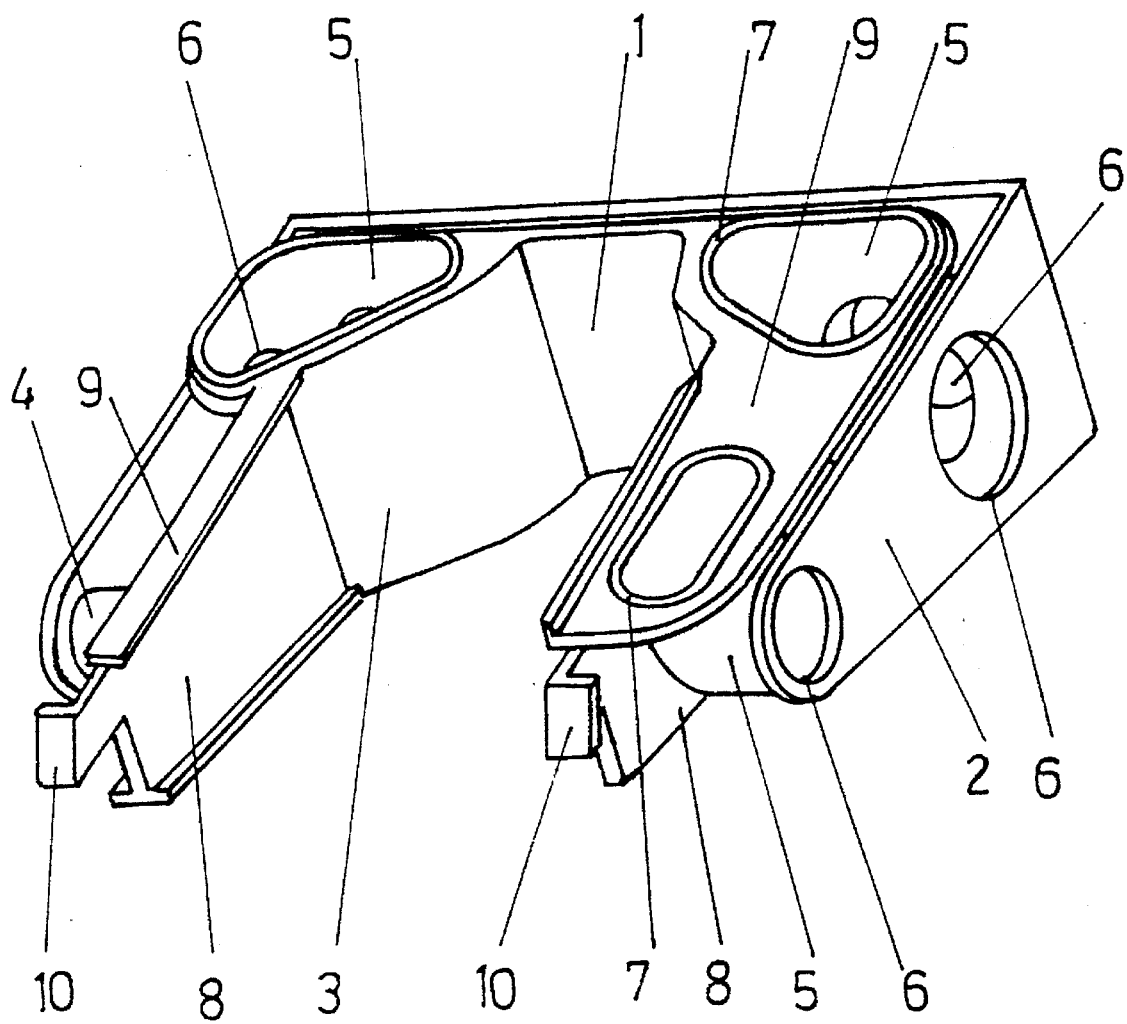
FIG. 1 shows an oblique view of a support.
Figure 2:
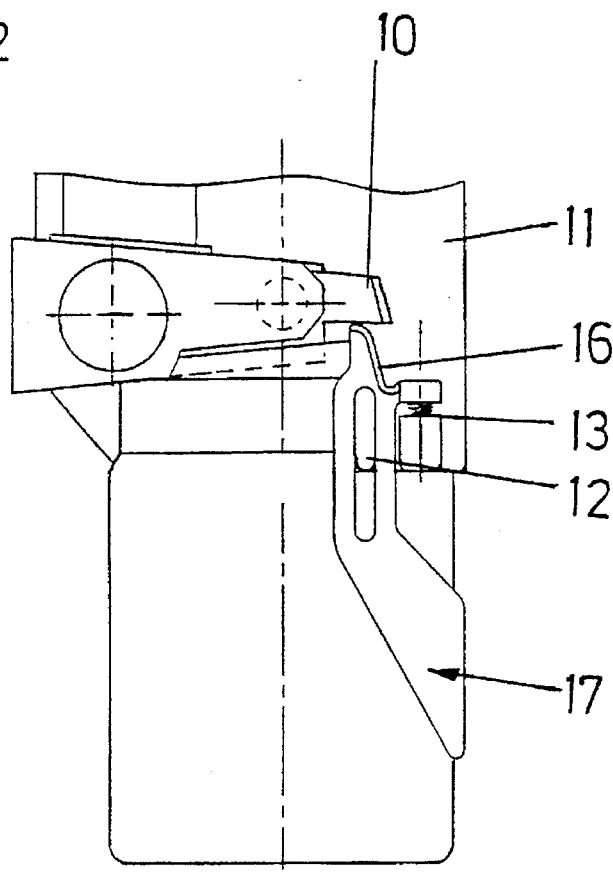
FIGS. 2 and 3 show side views of a separator inserted into the support, in the open and the locked position.
Figure 3:
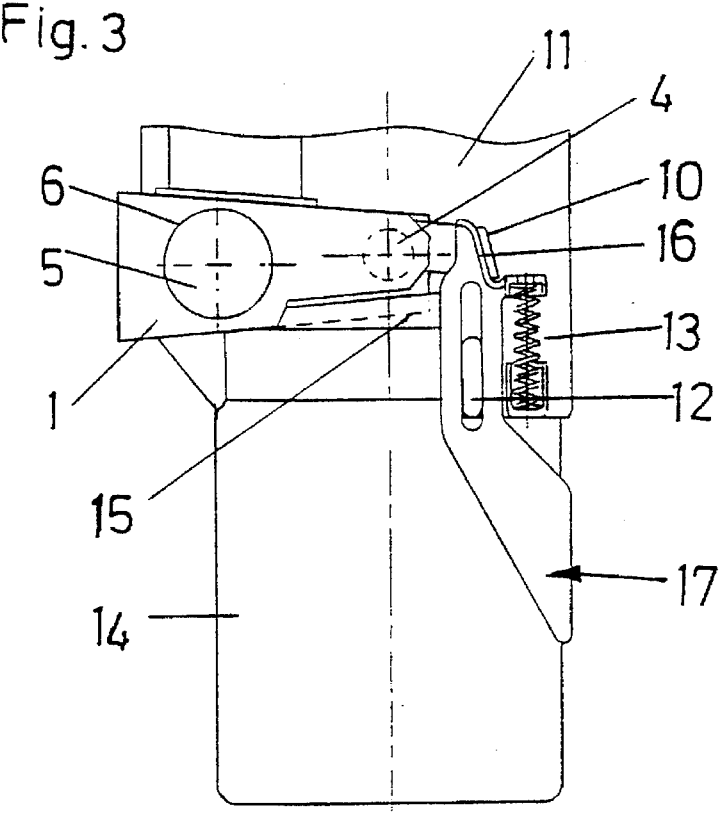

A support 1 for a separator that includes a centrifuge has a first U-shaped part 2 for mounting on a wall or the like, which is provided with line connections 6 to which various lines are connected when the separator is mounted (for mixture removed by suction, for mixture flowing out of a spit bowl, or clean air, or purified wastewater, etc.). A second, likewise U-shaped part 3 is disposed inside the first part 2 and is held on the first part 2 exclusively via vibration-damping intermediate components 4, 5 of an elastic material. The intermediate components 4, 5 in particular comprise a thermoplastic elastomer, and the intermediate components 5 form elastic tube sections.

At least the side ridges 8 of the inner U-shaped part 3 taper toward the free end. They are provided with ridges that can be engaged from behind and have tight-fit faces 9. Diametrically opposed retaining element 15 and tight-seat faces are provided on the separator housing 11, and the separator housing 11, slipped on into place, is locked to the inner part 3 by means of a tension lever closure 17. For that purpose, a handle is slidingly guided on the separator housing 11 in a slideway 12 along the collection container 14 for separated solids, this container being disposed removably below the housing 11, and is loaded by compression springs 13 fastened between the handle and the separator housing 11. Detent elements 16 on both sides of the handle engage tabs 10, disposed on the free ends of the ridges 8, from behind and lock the separator housing 11. At least some of the vibration-damping intermediate components are embodied as elastic tube sections 5, which open at the inner support part 3 in one of the tight-fit faces 9 and communicate at the outer support part 2 with the line Connections 6. Elastic tube sections 5 disposed in the corner region are bent like angle brackets and communicate with two line connections 6, of which one is embodied in the side ridge and the other is embodied in the center ridge of the outer support part 2. The line connections 6 are shown only schematically and may be embodied as plug-in sleeves or as slip-on socket pieces. If the side ridges of the outer support part 2 extend obliquely at an angle of 45°, then a 45° angle element can be positioned against the outside, so that a horizontal to vertical connection becomes possible by rotating the angle piece. Excess line connections 6 can be closed by a stopper or the like. The mouths of the elastic tube angles 5 in the tight-fit face 9 are preferably surrounded by seals 7, which are either formed by O-rings inserted into grooves or are made jointly with the intermediate components 4, 5 of the thermoplastic elastomer comprising them. An elastic plug connection is preferably embodied on the middle ridge of the inner support part 3, so that this connection like the flow paths between th tube angles 5 and the inlets or outlets of the separator are interrupted when the separator is removed from the vibration-damping inner support part 3 and are re-established when the separator is mounted on the inner support part 3 again.

We claim:

1. In combination with a dental separator of the type having at least one inlet and at least one outlet, a vibration-damping support for the dental separator, comprising:

first and second parts together defining the support, said first part being stationarily mountable, and said second part having the dental separator removably mounted thereon;

vibration-damping intermediate components connected between and joining said first and second parts;

the support being formed with line connections, and each of the at least one inlet and at least one outlet of the separator communicating with a respective line connection of the support.

2. The combination according to claim 1, wherein at least one of said vibration-damping intermediate components is a tube section connected between one of said line connections formed in said support, and an aperture formed in said second part provided for one of an inlet and an outlet of the dental separator.

3. The combination according to claim 2, wherein said tube section is elastic.

4. The combination according to claim 2, wherein said tube section is movably disposed on each of said first and second parts of the support.

5. The combination according to claims 1, wherein said first and second parts are substantially U-shaped, and said second part is nested inside said first part.

6. The combination according to claim 5, wherein said U-shaped second part for mounting the dental separator is defined with lateral ridges forming a lateral guide upon which the dental separator is slidable in drawer-like fashion.

7. The combination according to claim 6, wherein the dental separator has a housing, and which combination further comprises retaining tabs disposed on free ends defined on said U-shaped second part, and a clamping lever closure disposed on the housing of said dental separator for selectively engaging said retaining tabs.

8. The combination according to claim 6, wherein the dental separator has a housing, and wherein said lateral ridges of said U-shaped second part include tight-fit faces which converge in a direction of drawer-like sliding removal of the separator housing, and the combination further comprising elements formed on the separator housing for engaging said tight-fit faces.

9. The combination according to claim 8, wherein at least one of said vibration-damping intermediate components is a tube section connected between one of said line connections formed in said first part and an aperture formed in said second part provided for communicating with the dental separator, and wherein said tube section opens into one of said tight-fit faces.

10. The combination according to claim 9, wherein said at least one elastic tube section is disposed in a corner region of the support and communicates with two line connections pointing in mutually divergent directions.

11. The combination according to claim 1, wherein the support is manufactured in one piece from two plastics with mutually different properties, and said vibration-damping intermediate components are formed from a thermoplastic elastomer.

* * * * *